United States Patent
Winter et al.

(10) Patent No.: US 6,342,649 B1
(45) Date of Patent: Jan. 29, 2002

(54) METHOD FOR REMOVING ETHYLBENZENE FROM A PARA-XYLENE FEED STREAM

(75) Inventors: George R. Winter, Mt. Prospect, IL (US); Zvi Merchav, Haifa (IL)

(73) Assignee: Denim Engineering, INC, Fond du Lac, WI (US)

(*) Notice: Subject to any disclaimer, the term of this patent is extended or adjusted under 35 U.S.C. 154(b) by 0 days.

(21) Appl. No.: 08/437,986

(22) Filed: May 10, 1995

(51) Int. Cl.$^7$ .............................. C07C 5/22; C07C 4/12
(52) U.S. Cl. ...................... 585/477; 585/479; 585/486
(58) Field of Search ...................... 585/316, 319, 585/321, 477, 479, 486

(56) References Cited

U.S. PATENT DOCUMENTS

| | | | | |
|---|---|---|---|---|
| 2,719,183 A | * | 9/1955 | Boedecker et al. | 855/477 |
| 2,838,581 A | * | 6/1958 | Bloch | 585/321 |
| 3,691,247 A | * | 9/1972 | Billings | 585/479 |
| 3,702,347 A | * | 11/1972 | Adams | 585/479 |
| 3,856,873 A | * | 12/1974 | Burress | 585/486 |
| 3,959,978 A | * | 6/1976 | Lindley et al. | 585/479 |
| 4,101,597 A | * | 7/1978 | Breckenridge | 585/321 |
| 4,163,028 A | * | 7/1979 | Tabak et al. | 585/486 |
| 4,188,282 A | * | 2/1980 | Tabak et al. | 585/470 |
| 4,218,573 A | * | 8/1980 | Tabak et al. | 585/486 |
| 4,236,996 A | * | 12/1980 | Tabak et al. | 585/486 |
| 4,482,773 A | * | 11/1984 | Chu et al. | 585/479 |
| 4,654,456 A | * | 3/1987 | Nimry | 585/477 |
| 4,697,039 A | * | 9/1987 | Schmidt | 585/477 |
| 4,723,050 A | * | 2/1988 | Butler et al. | 585/477 |
| 4,783,568 A | * | 11/1988 | Schmidt | 585/477 |
| 5,030,788 A | * | 7/1991 | Amelse et al. | 585/477 |
| 5,329,060 A | * | 7/1994 | Swift | 585/479 |
| 5,847,256 A | * | 12/1998 | Ichioka et al. | 585/486 |
| 5,977,420 A | * | 11/1999 | Abichandani et al. | 585/479 |

FOREIGN PATENT DOCUMENTS

| | | | | |
|---|---|---|---|---|
| GB | 996575 | * | 6/1965 | 585/479 |
| GB | 1009555 | * | 11/1965 | 585/321 |
| GB | 1 258 292 | * | 12/1971 | 585/321 |
| GB | 2052554 | * | 1/1981 | 585/486 |
| WO | 84/01375 | * | 4/1984 | 585/477 |

* cited by examiner

*Primary Examiner*—Mark L. Bell
*Assistant Examiner*—J. Pasterczyk
(74) *Attorney, Agent, or Firm*—Kajane McManus

(57) ABSTRACT

The method for removing ethylbenzene from a feed stream for use in producing para-xylene product, the stream containing para-xylene, ortho-xylene, meta-xylene and ethylbenzene. The method incorporates provision of a reactor unit used in a pretreatment step, the reactor containing an isomerization catalyst in an amount sufficient to convert substantially all the ethylbenzene in the feed stream to benzene, and provides for removal of the converted benzene from the stream prior to cyclic retreatments of the stream by a para-xylene separator and an isomerization unit, respectively.

6 Claims, 1 Drawing Sheet

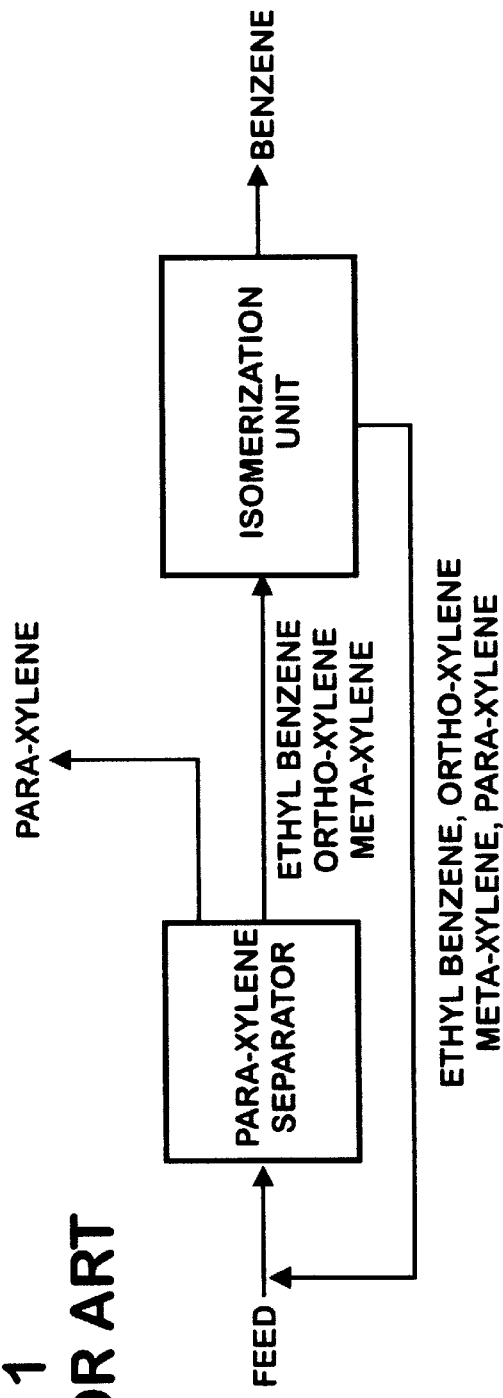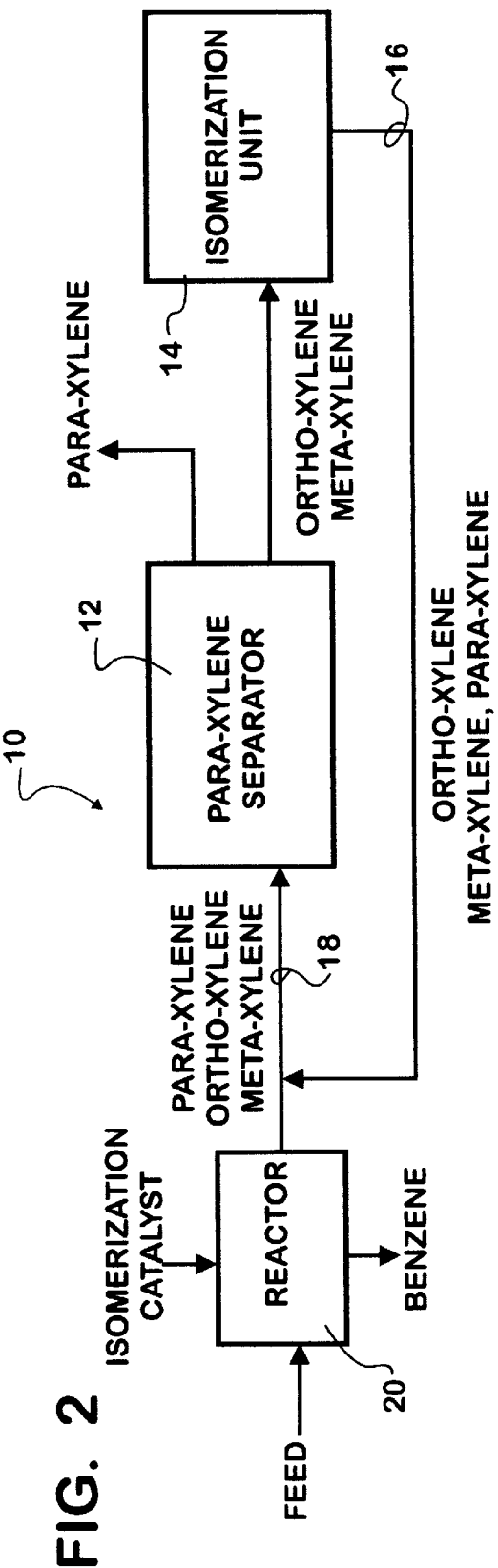
FIG. 1
PRIOR ART
FIG. 2

METHOD FOR REMOVING ETHYLBENZENE FROM A PARA-XYLENE FEED STREAM

BACKGROUND OF THE INVENTION

1. Field of the Invention

The present invention provides a method and apparatus for removing ethylbenzene from a para-xylene feed stream. More particularly the method includes the pretreatment step of processing the feed stream through a reactor comprising a small version of an isomerization unit within which an isomerization catalyst is provided, the catalyst causing a high level of conversion of ethylbenzene to benzene without producing side reactions, such as cracking of xylenes. The benzene is then removed from the feed stream prior to cyclic para-xylene separation and isomerization, respectively. Although the apparatus and method are proposed for use in para-xylene production, they are equally well suited to use in production of ortho-xylene and meta-xylene.

2. Description of the Prior Art

Para-xylene is a precursor in the manufacture of polyesters, which are used in creating clothing and other synthetic materials. Most para-xylene is produced in oil refineries downstream of catalytic reformers which manufacture gasoline.

Gasoline contains a mixture of hydrocarbons including C8 aromatics. The C8 aromatics include four chemical compounds: para-xylene, meta-xylene, ortho-xylene and ethylbenzene. The para-xylene is isolated from the other C8 aromatics by one of two physical separation processes, crystallization or molecular sieve technology. Once the para-xylene has been removed from the mixture of C8 aromatics, the remaining mixture of meta-xylene, ortho-xylene and ethylbenzene is sent to an isomerization unit where further para-xylene is created by returning the xylene mixture to an equilibrium concentration, with the new ratio of xylene isomers being returned to the separation unit for reprocessing.

The concentration of para-xylene in the recycled feed to the separation unit determines the efficiency of the operation. For example, in a crystallizer, the mother liquor contains about 10% para-xylene. Therefore, if the recycled feed stream contains 19%, about 9% will be extracted and 10% will not be extracted. However, if the recycled feed stream contains 21% para-xylene, the production rate increases substantially due to an 11% extraction. Thus, increasing the para-xylene in the recycled feed stream from 19% to 21% will increase the plant capacity by approximately 11/9, or 20%.

In modern units, the ethylbenzene is dealkylated to benzene in the isomerization unit. This reaction proceeds at 50 to 60% conversion per pass. Thus, the recycled feed stream provided to the separation unit always contains a substantial amount of ethylbenzene. This ethylbenzene builds up in the mother liquor/recycled feed stream combination causing processing equipment to be larger than necessary to merely process the para-xylene, ortho-xylene and meta-xylene. Since the recycled feed stream to the separation unit contains approximately 20% para-xylene, the mother liquor will contain the unextracted para-xylene plus the remainder of the chemicals which are not para-xylene. Thus, the mother liquor/recycled feed stream becomes quite large, requiring large processing equipment. For a crystallizer, the mother liquor recycle is six times para-xylene flow rate. In a molecular sieve extraction unit, the recycle is about four times the para-xylene flow rate. If ethylbenzene were removed from the feed in an initial pretreatment step, the remaining stream would only have para-xylene, meta-xylene and ortho-xylene therein. Parameters of conditions required for an isomerization reaction to the point of equilibrium in the conversion of the meta-xylene and ortho-xylene to a combination thereof with created para-xylene become less severe if little or no ethylbenzene is fed to the isomerization unit. The severity is reduced because the point of equilibrium now revolves around only three xylenes, with no ethylbenzene contaminant needing to be considered. Also, the mother liquor flow rate per unit of para-xylene production is reduced, saving energy required for processing.

SUMMARY OF THE INVENTION

Accordingly, removing substantially all of the ethylbenzene from the feed stream would provide a considerable advantage inasmuch as the production of para-xylene would increase proportionally with the concentration of the para-xylene in the recycled feed stream and the isomerization unit would be more efficient in processing due to lack of ethylbenzene in the feed stream thereto.

Such removal of ethylbenzene from the feed stream is accomplished by the method and apparatus of the present invention.

BRIEF DESCRIPTION OF THE DRAWINGS

FIG. 1 is a block diagram of a prior art method and apparatus for obtaining para-xylene product.

FIG. 2 is a block diagram of the method and apparatus of the present invention.

DESCRIPTION OF THE PREFERRED EMBODIMENT

Turning now to FIG. 1 there is illustrated therein a prior art method and apparatus for the production of para-xylene product. As shown, a feed stream comprising a mixture of eight-carbon (C8) aromatics including para-xylene, meta-xylene, ortho-xylene and ethylbenzene is fed to a para-xylene separator. From the separator, existing para-xylene is shunted into a collection unit and ethylbenzene, ortho-xylene and meta-xylene are passed on to an isomerization unit. In this isomerization unit, the ethylbenzene is dealkylated to benzene with the reaction proceeding at a 50 to 60% conversion per pass. The converted benzene is removed from the stream and the remainder of the recycle feed stream, now containing somewhere in the range of 40 to 50% of the previous amount of ethylbenzene therein, together with equilibrium amounts of ortho-xylene, meta-xylene and para-xylene formed in the isomerization unit, are sent back to the feed line via which the feed is being fed into the para-xylene separator. Cyclic separation and isomerization continues until a majority of the unextracted para-xylene is captured as para-xylene product. It will be understood that the ethylbenzene builds up in the recycle feed stream since the recycle stream to the separation unit typically contains 20% para-xylene with the feed containing unextracted para-xylene plus the 80% comprising the other C8 aromatics defined above. Thus, the recycle stream is quite large. Inasmuch as the recycle stream is quite large, processing equipment for this process must be extremely large to accommodate the flow therethrough that is being created. In a crystallization separator system, the mother liquor recycle is six times the para-xylene flow rate while in a molecular sieve extraction unit the recycle is about four times the para-xylene flow rate. Thus, if one were capable of removing the ethylbenzene from the mother liquor in a pretreatment step, rather than removing it in the isomerization unit, approximately 15% of the feed stream bulk could be eliminated at the beginning of the process, a greater concentration of para-xylene would be obtained, and the isomerization unit as well as the separation unit would both work more efficiently in processing. Not only would this increase the efficiency, requiring significantly decreased energy for processing, but further the size of the units could be decreased substantially while maintaining increased processing. Still further, operating conditions in the isomerization unit would be less severe, significantly increasing yield.

Thus, it is proposed as shown in FIG. 2, to produce a method and apparatus for the production of para-xylene product wherein substantially all of the ethylbenzene is converted to benzene in a pretreatment, or primary step, distilled, and removed with only para-xylene, ortho-xylene and meta-xylene being fed into the remainder of the processing complex. This apparatus is generally identified by the reference numeral 10. Although the instant disclosure is provided using para-xylene as the chosen product, this is not to be construed as limiting inasmuch as the apparatus 10 and method would be applicable to the production of ortho-xylene and/or meta-xylene and/or para-xylene. For purposes of brevity, application to a para-xylene production complex is set forth as a primary embodiment and a broader scope application would be feasible without undue experimentation. As shown, the apparatus 10 includes a para-xylene separator 12 which functions in the normal manner as described above and an isomerization unit 14 which functions in a more efficient manner. In this respect, inasmuch as there is almost no ethylbenzene being fed into the isomerization unit 14, none of the C8 aromatics being fed thereinto are required to be eliminated from the feed stream. Thus, the isomerization unit 14 here strictly functions in a manner to produce para-xylene from ortho-xylene and meta-xylene fed thereto. Obviously, inasmuch as several passes through the isomerization unit 14 will now be, and always have been, required, there will be an equilibrium concentration of meta-xylene and ortho-xylene fed back into the recycle line 16 leading back to a combined feed line 18 feeding the para-xylene separator 12. However, due to increased efficiency, the amount of meta-xylene and ortho-xylene will be significantly reduced, with a greater amount of para-xylene product being available in the feed stream fed into the feed line 16, and there will be substantially no ethylbenzene traveling back into the feed line 16.

The ethylbenzene is proposed to be removed from the feed stream going into the para-xylene separator 12 by the provision of a pretreatment unit or reactor 20 within the feed line 18 for the mother liquor feed. This pre-treatment unit 20 comprises a small version of an isomerization unit and includes therein a large amount of an isomerization catalyst, one form of which is sold under the mark I-100 by UOP, Inc. of Des Plaines, Ill. Other companies that sell similar catalysts are Criterion Co. of Houston, Tex., Englehardt Co., of New York, N.Y., IFP (Institute de Francaise Petroleum), Paris, France, and Toray (Toyo Rayon Company) of Tokyo, Japan. It is believed that such catalyst is created of platinum and chloride supported on alumina. Further, a catalyst which would be based on a molecular sieve base would also be functional, such catalyst being available through Mobil Oil Corporation of Princeton, N.J.

It has been found through empirical testing using the I-100 catalyst that approximately 90% conversion of ethylbenzene may be obtained in the pre-treatment unit 20 at a liquid hourly space velocity of 1 to 4, as is known. Because the feed stream rate is much lower than the recycle stream rate, the catalyst volume may be large in comparison to the hydrocarbon rate, such large volume of catalyst permitting a high level ethylbenzene conversion while avoiding side reactions such as cracking of xylenes.

Based on calculations founded on the empirical testing performed, the following advantages, based on separation technique, are expected:

1. Molecular Sieve Technology

For a para-xylene unit using molecular sieve technology making 20 MT/hr of para-xylene product, the total flow rate to the para-xylene separation unit will be 86.3 MT/hr, and the feed rate to the isomerization unit will be about 60 MT/hr.

Using the apparatus 10 and method defined above and holding constant the feed rate to the para-xylene separation unit, para-xylene production will increase to 27.2 MT/hr, an increase of 36%. At the current market price of $2,000/MT, the incremental production is worth over $115 million per year:

(7.2 MT/hr)(8,000 hrs/yr)($2,000/MT)=$115,200,000/yr.

Because the feed to the isomerization unit 14 will decrease to 55.3 MT/hr, the energy cost will decrease by almost 8%:

(55.3 MT/hr)/(59.8 MT/hr)=92%

At an energy cost of roughly $100/MT of para-xylene presently existing, this would be worth almost $1,000,000 per year:

($100/MT)(20 MT/hr)(8,000 hrs/yr)(8%)=$1,280,000/yr pos

2. Crystallization Technology

If the para-xylene separation uses crystallization technology, the circulation numbers change, but the results are just as dramatic. Holding the circulation rate at about 60 MT/hr, the production of para-xylene will be about one-half of that produced by the molecular sieve unit, or 10 MT/hr.

By use of the apparatus 10 and method defined above, the production of para-xylene will increase to 13.6 MT/hr, half of the above numbers. Likewise, the benefits will be about half of the dollars calculated above.

It will also be understood that most feed stocks for para-xylene production are prepared from low pressure reformers, or high pressure reformers followed by extraction. In low pressure reformers, non-aromatics in the xylene volatility range are reacted to either aromatics or to light non-aromatics. In reformers operating above 100 psig, the non-aromatics do not react to near extinction. As a result, the non-aromatics must be separated from the aromatics by extraction.

A further strong advantage of apparatus 10 and method is that hydrocracking of the non-aromatics to light compounds occurs so that they can easily be removed from the xylenes.

As defined above, the method and apparatus 10 provide a number of advantages, some of which have been described above and others of which are inherent in the invention. Also modifications may be proposed without departing from the teachings herein. For example, if the desired product were ortho-xylene, the separator used would be in the form of a distillation tower, which is considered within the scope of the invention. Further, if a functionally equivalent catalyst is used in place of an isomerization catalyst, this would also be construed as within the scope of the invention. Accordingly, the scope of the invention is only to be limited as necessitated by the accompanying claims.

We claim:

1. A method for producing at least one xylene isomer product from a feed stream comprising at least ortho-xylene, meta-xylene, ethylbenzene and para-xylene, the method comprising the steps of:

starting with a feed stream comprising at least para-xylene, meta-xylene, ortho-xylene and ethylbenzene;

feeding the feed stream into a pretreatment unit having an isomerization/cracking catalyst therein in an amount sufficient to cause an approximately 90% conversion of ethylbenzene to benzene and removing the converted benzene from the stream;

passing the resulting stream to a xylene isomer specific separator;

removing a desired xylene isomer from the resulting stream;

passing the stream through an isomerization unit having an isomerization/cracking catalyst therein;

creating a stream having an equilibrium amount of xylene isomers exiting the isomerization unit; and passing the stream back into the xylene isomer specific separator for processing.

2. The method of claim 1 wherein the separator is a crystallizer.

3. The method of claim 2 wherein the stream exiting the isomerization unit is returned to said separator.

4. The method of claim 1 wherein the separator is a molecular sieve.

5. The method of claim 4 wherein the stream exiting the isomerization unit is returned to said separator.

6. A method for producing substantially pure mixed xylenes from an unextracted mixture comprising eight carbon aromatics, the method comprising the steps of:

starting with a feed stream comprising at least para-xylene, meta-xylene, ortho-xylene, ethylbenzene and non-aromatic hydrocarbons;

feeding the feed stream into a pretreatment unit having an isomerization/cracking/hydrocracking catalyst therein in an amount sufficient to cause an approximately 90% conversion of ethylbenzene to benzene and removing the converted benzene from the stream; and further causing conversion of non-aromatic compounds to hydrocarbons lighter than ethylbenzene within the pretreatment unit and removing the hydrocarbons lighter than ethylbenzene from the stream.

\* \* \* \* \*